United States Patent
Meir et al.

(10) Patent No.: US 7,659,111 B2
(45) Date of Patent: Feb. 9, 2010

(54) METHOD FOR FREEZING VIABLE CELLS

(75) Inventors: Uri Meir, Kibbutz Bet Hashita (IL); Yoram Amsalem, Gan Yavneh (IL); Yehudit Natan, Holon (IL); Amir Arav, Tel Aviv (IL)

(73) Assignee: Core Dynamics Limited, Hamilton (BM)

( * ) Notice: Subject to any disclaimer, the term of this patent is extended or adjusted under 35 U.S.C. 154(b) by 450 days.

(21) Appl. No.: 10/488,414

(22) PCT Filed: Sep. 5, 2002

(86) PCT No.: PCT/IL02/00738

§ 371 (c)(1), (2), (4) Date: Mar. 2, 2004

(87) PCT Pub. No.: WO03/020874

PCT Pub. Date: Mar. 13, 2003

(65) Prior Publication Data

US 2004/0191754 A1    Sep. 30, 2004

Related U.S. Application Data

(60) Provisional application No. 60/391,595, filed on Jun. 27, 2002.

(51) Int. Cl.
   *C12M 1/02* (2006.01)
   *F25D 13/06* (2006.01)
(52) U.S. Cl. .................. 435/307.1; 435/2; 435/260; 435/298.2; 435/303.2; 435/809; 62/63; 62/380; 62/382
(58) Field of Classification Search .......... 435/2, 435/307.1, 260, 298.2, 303.2, 809; 62/63–65, 62/374, 380, 382
See application file for complete search history.

(56) References Cited

U.S. PATENT DOCUMENTS

| 3,347,745 | A | * | 10/1967 | Rinfret et al. ............... 62/67 |
| 4,857,319 | A |   | 8/1989  | Crowe et al. |
| 4,874,690 | A |   | 10/1989 | Goodrich, Jr. et al. |
| 5,059,518 | A |   | 10/1991 | Kortright et al. |
| 5,071,598 | A |   | 12/1991 | Baldeschwieler et al. |
| 5,364,756 | A |   | 11/1994 | Livesey et al. |
| 5,873,254 | A |   | 2/1999  | Arav |
| 6,073,540 | A | * | 6/2000  | Garrett ..................... 99/330 |

FOREIGN PATENT DOCUMENTS

| JP | 2000-189155 A2 | 7/2000 |
| RU | 1806692 A1 | 4/1993 |

OTHER PUBLICATIONS

Kusakabe, H., et al., "Maintenance of genetic integrity in frozen and freeze-dried mouse spermatozoa", *Proc Natl Acad Sci U S A*, vol. 98, No. 24, pp. 13501-13506, (2001).

* cited by examiner

*Primary Examiner*—William H Beisner
(74) *Attorney, Agent, or Firm*—The Nath Law Group; Susanne M. Hopkins; Ari G. Zytcer

(57) ABSTRACT

A method and a device for improved freezing of biological containing living cells is disclosed. Directional cooling coupled with agitation, preferably rotation, of the vessel containing the biological sample allows for the freezing of large volume samples at much greater rates than before. Whether a sample is large or not, the greater thermal homogeneity during the freezing process as well as the resulting crystal morphology yield a frozen sample which is exceptionally suited for lyophilization.

27 Claims, 3 Drawing Sheets

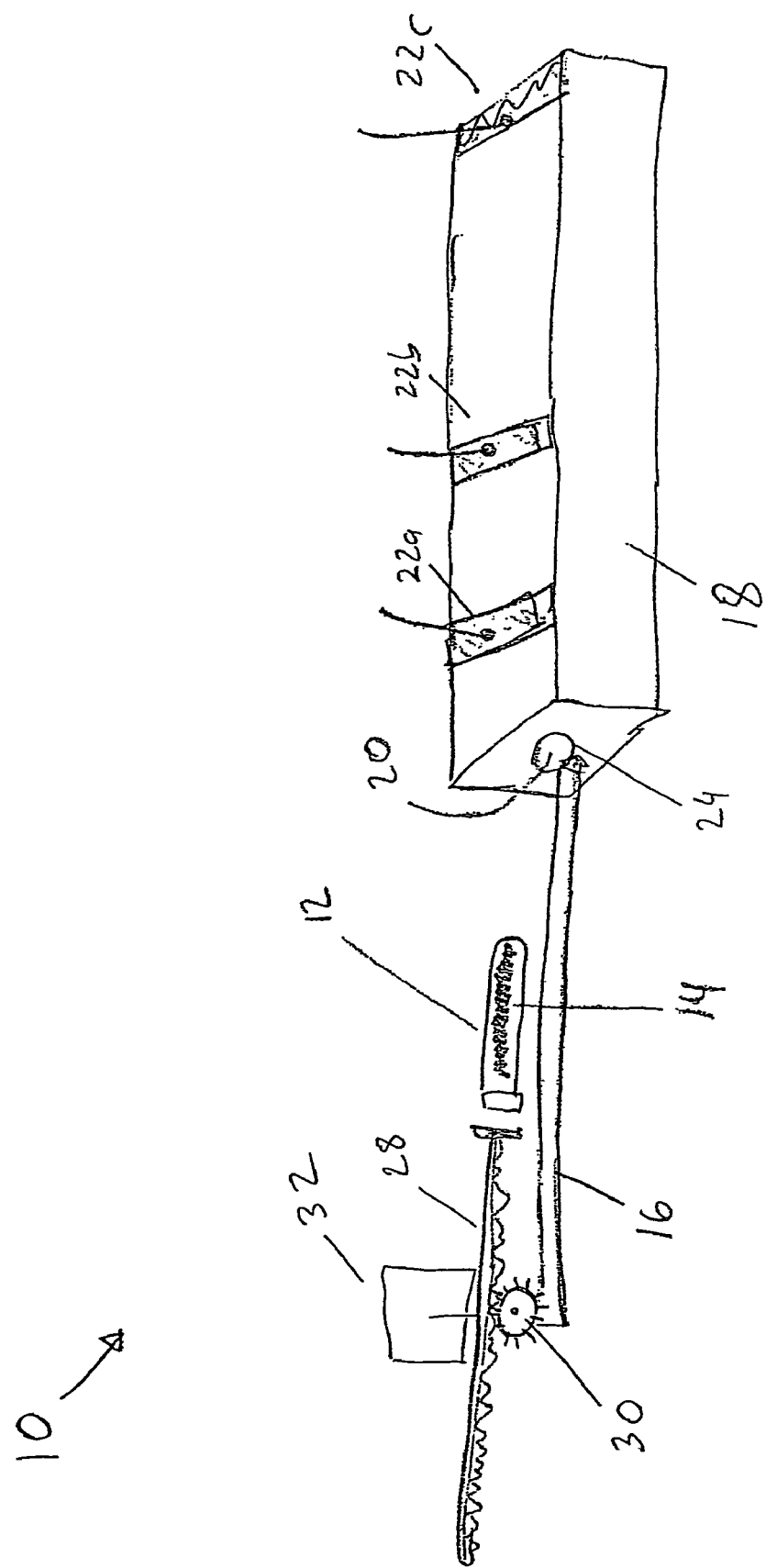

METHOD FOR FREEZING VIABLE CELLS

RELATED APPLICATIONS

This application claims benefit of U.S. Provisional Application No. 60/391,595 filed Jun. 27, 2002, and of PCT IL02/00738 filed Sep. 5, 2002.

FIELD OF THE INVENTION

The present invention relates to the storage of living cells and in particular relates to a method of and device for freezing living cells. The method can be applied to freeze high volume samples or for the freezing as a preparatory step preceding lyophilization.

BACKGROUND OF THE INVENTION

There is often a need to store viable cells for extended periods of time. It is most preferred that the cells be held in a state of suspended animation, a state wherein cell metabolism is entirely stopped. When needed, the cells are reanimated and used. Cells such as spermatozoa, blood and blood products are amongst the cell types for which long term storage is desired.

A generally accepted way of storing cells in a state of suspended animation is cryopreservation. Most simply, a sample containing viable cells is quickly cooled, for example by immersion in liquid nitrogen, to freeze the sample. When thawed under carefully controlled conditions acceptable levels of post-thaw cell viability are achieved.

The greatest practical disadvantage of cryopreservation of cells involves the difficulties in maintaining the frozen state. Refrigeration at cryogenic temperatures of 198 K is necessarily expensive (excepting in the Antarctic) and not a perfect solution as biological activity does not cease until about 143 K. The bulk of the required refrigeration systems renders cryopreserved cells not easily transportable.

An additional method for storing cells in a state of suspended animation involves removing a significant proportion of water from the cells (drying). The greatest advantage of drying cells is that dry cells can potentially be stored at close to room temperatures without requiring bulky and expensive storage devices. Typically, cells are air-dried: the cells in solution are spread out in a thin layer and water allowed to evaporate. Although clearly there is no danger of ice crystal formation damaging the cells, the fact that the drying process occurs at a temperature of at least above. 273 K where cell metabolism is active is a great disadvantage. Further, air drying has not been shown to be a practical method for the preservation of large-volume samples. Post-rehydration viability of air-dried cells is incidental at best. Apparently, either the air-drying process or the rehydration process causes cytolysis.

A number of researchers have found methods of improving post-rehydration viability of air-dried cells by the addition of cell membrane stabilizers. Such stabilizers added to a buffered cell-containing solution improve post-rehydration viability.

Another approach for drying cells involves freeze-drying. The simplest methods involve lyophilization of a frozen sample. Post-rehydration viability is poor.

It has been found that an effective methods of increasing post-thaw or post-rehydration viability of frozen or freeze-dried cells, respectively, is the addition of cryoprotectants, substances that protect cell membranes from the effects of freezing.

One group of cryoprotectants, termed permeating cryoprotectants are antifreeze molecules and includes dimethyl sulfoxide (DMSO), glycerol and related polyhydril alcohols (e.g. propylene or ethylene glycol).

Another group of cryoprotectants termed non-permeating or extracellular cryoprotectants, bind to membrane lipids. The membrane lipids are stabilized, thus preserving cell-structure integrity. Such cryoprotectants include proline and sugars (e.g. glucose). Crowe (in U.S. Pat. No. 4,857,319) has taught that trehalose is an exceptionally good cryoprotectant.

The disadvantages of using cryoprotectants are manifold. Different cell types require different cryoprotectants at different concentrations. Thus the use of cryoprotectants is not a general method but rather requires a complex and time-consuming optimization step. Second, rehydration and thawing must be very carefully due to the effect of osmotic pressure resulting from the presence of cryoprotectants in solution. Lastly, upon rehydration or thawing, the cells are found in an "unnatural" solution which must be purified or modified before being used.

Kusakabe et al. ("Maintenance of genetic integrity in frozen and freeze-dried mouse spermatozoa" *Proc. Natl. Acad. Sci., U.S.A.* Nov. 20, 2001, 98(24), 13501-13506) has convincingly demonstrated that freeze-drying is a potentially successful strategy for the long term storage of cells. Mouse spermatozoa in a buffered solution without cryoprotectants were freeze dried by immersion in liquid nitrogen followed by 4 hours lyophilization. The freeze dried samples were stored at 277 K for up to 56 days. The results indicate a high level of DNA integrity after rehydration. However, the usefulness of the teachings of Kusakabe et al. is limited by the fact that the cells were lyophilized in 0.1 ml portions. One skilled in the art would remain unconvinced of the potential of this method for the preservation of cells on a larger scale.

In U.S. Pat. No. 5,873,254. which is incorporated by reference for all purposes as if fully set forth herein, is described an innovative method for the freezing of biological samples by directional cooling. Schematically depicted in FIG. 1 is a device 10 used to realize the teachings of U.S. Pat. No. 5,873.254. In FIG. 1A, a vessel 12 holding a biological sample 14 lays on a track 16. Track 16 leads from the surroundings into a cooling device 18. Cooling device 18 is substantially a block of a thermally conductive material having a tunnel 20 through which vessel 12 can pass when guided along track 16. In cooling device 18 is maintained a temperature gradient by the use of a plurality of cooling elements 22a, 22b and 22c. The temperature gradient is oriented so that there is a temperature gradient parallel to tunnel 20. The temperature of cooling device 18 at entrance 24 of tunnel 20 is typically roughly the temperature of sample 14 at the beginning of the freezing process. Exit 26 of tunnel 20 is cooler than entrance 24. A toothed rod 28, a gear 30, configured to engage rod 28, and an electrical motor 32, configured to rotate gear 30, are all elements of a mechanism configured to push vessel 12 into and through tunnel 20 at a controlled rate.

When it is desired to freeze biological sample 14, motor 32 is activated causing rod 28 to push vessel 12 into cooling device 18 through tunnel 20, FIG. 1B. Throughout the travel of biological sample 14 through tunnel 20, each portion of biological sample is cooled at a similar rate, but at any given moment the temperature of biological sample near the leading end 34 of vessel 12 is lower then that of biological sample near the following end 36 of vessel 12. A cooling front is formed inside biological sample 14, the cooling front traveling from leading end 34 towards following end 36, in parallel to the motion of vessel 12 along track 16. Biological sample 14 found in a given cross-section perpendicular to the motion of vessel 12 along track 16 is substantially homogenous in temperature. Through biological sample 14 is a temperature gradient parallel to track 16, the temperature gradient substantially mirroring the temperature gradient found along track 16.

Practically, it has been found that to prevent supercooling of biological sample 14 (and the concomitant uncontrolled and inhomogeneous freezing rate, see U.S. Pat. No. 5,873,254) it is necessary to "seed" biological sample near leading end 34 before entering tunnel 20. Seeding is done, for example, by applying liquid nitrogen to leading end 34.

An important parameter when applying the method of U.S. Pat. No. 5,873,254 is the cooling rate. The cooling rate C (in units of ° C./min) is determined by the temperature gradient G (in units of ° C./mm) alone track 16 and the rate of advancement of the cooling front P (in units of mm/sec) through biological sample 14, determined by the speed which vessel 12 travels through tunnel 20.

Cells in cryoprotectant-containing samples have exceptional post-thaw viability when frozen according to the method of U.S. Pat. No. 5,873,254, for example by using a device such as device 10. It is important to note that when a biological sample is lyophilized subsequent to freezing according to the method of U.S. Pat. No. 5,873,254, post-rehydration cell viability is insufficient.

A practical disadvantage of the method of U.S. Pat. No. 5,873,254 arises from the relatively limited amounts of sample that can be frozen at any one time. Experimentally it has been found that post-rehydration viability decreases when large volumes (generally greater than 1 ml) are frozen.

It would be highly advantageous to have a method of freezing large volume samples containing living cells. It would be exceptionally advantageous if such a method froze the sample in a way as to allow high post-rehydration post-lyophilization viability. It would be advantageous if such a method did not require the use of cryoprotectants.

SUMMARY OF THE INVENTION

The above and other objectives are achieved by the innovative method of freezing biological samples and use of the innovative device provided by the present invention.

The method of the present invention involves directional cooling of a biological sample, substantially as described hereinabove and in U.S. Pat. No. 5,873,254, but unique in that as biological sample containing vessel advances through the thermal gradient, the vessel is agitated. The preferred agitation mode is rotation, the axis of rotation preferably being substantially perpendicular to the direction of advancement.

According to the teachings of the present invention there is provided a method for freezing cells including confining a sample in a vessel (the vessel having a leading end and a terminal end, the sample containing the cells and having a freezing point) and gradually cooling the sample to below the freezing point so as to generate a temperature gradient in the sample, where during cooling the leading end is cooler than the terminal end so as to generate a freezing front moving from the leading end towards the terminal end where during the gradual cooling the vessel is agitated.

According to a feature of the present invention the agitation is rotation of the vessel about an axis, the axis being substantially perpendicular to the freezing front.

According to a feature of the present invention the vessel is not completely filled with sample, preferably being less than about 90% filled, more preferably less than about 50% filled, and even more preferably less than about 30% filled. The partial filling of the vessel by sample leads to a frozen sample with a large surface area and a crystal structure that allows for simple lyophilization and for exceptional post-rehydration viability of thus freeze-dried cells.

According to the teachings of the present invention there is provided a method for freeze-drying cells by freezing a sample containing the cells as described above and subsequently lyophilizing the frozen sample.

According to the teachings of the present invention there is provided a method for storing viable freeze dried cells by freeze-drying a sample containing the cells as described above and subsequently storing the sample at a storage temperature greater than about 193 K, greater than about 253 K and even greater than about 273 K for a period of time greater than 1 day, greater than one week and even greater than 6 weeks.

According to a feature of the present invention to the sample, before freeze-drying is added a cryoprotectant, that is solid at the storage temperature. Preferably the cryoprotectant is trehalose.

The device of the present invention is substantially a device for directional cooling of biological samples as described in U.S. Pat. No. 5,873,254 but additionally including a means of agitating the vessel in which the biological sample to be frozen is contained.

Agitation of the sample can be performed in a large number of ways. Conceivably shaking, vibrating, rocking, rolling can all be implemented as agitation methods to ensure that the biological sample is mixed during the freezing process and as a result the thermal homogeneity in the cooling front. Simplest to implement is rotation of the vessel, especially when the axis of rotation is parallel to the direction of advancement and thus perpendicular to the cooling front. Intuitively it seems that rotation perpendicular to the cooling front is the agitation method that allows for the greatest thermal homogeneity within the cooling front without disrupting the temperature gradient within the biological sample.

The word vessel as used herein is non-limiting and refers to a vessel in the usual sense of the word and includes such objects as bags, bottles, flasks, jars, tubes, boxes, sacks and other containers.

While not wishing to be held to any one theory, it is believed that the agitation of the sample during directional cooling modifies the thermal homogeneity during the freezing process as well as the crystal morphology. Less cell damage occurs during the freezing process. When the sample does not entirely fill the test tube, the total surface area of the frozen sample is increased, allowing quick and efficient lyophilization without damaging cell membranes.

Thus according to the teachings of the present invention is provided a device for freezing a sample (especially a living cell containing sample of biological origin) including a vessel for containing the sample, a mechanism for moving said vessel along a track and a refrigeration means for imposing a laterally variable temperature gradient along the track the refrigeration means including a plurality of thermally conductive blocks substantially enclosing the track where the device also includes a a means of agitating the vessel when moving along the track.

According to a feature of the device of the present invention, the vessel is a tube with a diameter of greater than about 6 mm.

According to a further feature of the device of the present invention the means of agitating the vessel includes a motor, such as an electrical motor. According to a feature of the device of the present invention the means of agitating the vessel includes a control device to vary the intensity of agitation of the vessel.

According to a still further feature of the present invention, the means of agitating the vessel are in fact means of rotating the vessel. Preferably, rotations is around an axis substantially parallel to the track, that is substantially perpendicular to a cold front generated inside the sample when the device is operated (vide infra). According to a feature of the present invention the rotation is caused by a motor, such as an electrical motor. Preferably the device of the present invention is fitted with a control device to vary the rate of rotation of the vessel.

It is important to note that the method and device of the present invention are developed for and described herein as relates to samples of a biological origin containing living cells. However as is clear to one skilled in the art, the teachings of the present invention can be applied to and include other complex structures that are susceptible to freeze-damage such as (but not limited to) proteins, nucleic acids, liposomes, micelles, vesicles, cells, viruses, organs and organisms.

BRIEF DESCRIPTION OF THE DRAWINGS

The invention is herein described, by way of example only, with reference to the accompanying drawings, wherein.

DETAILED DESCRIPTION OF THE INVENTION

Figure 1B:
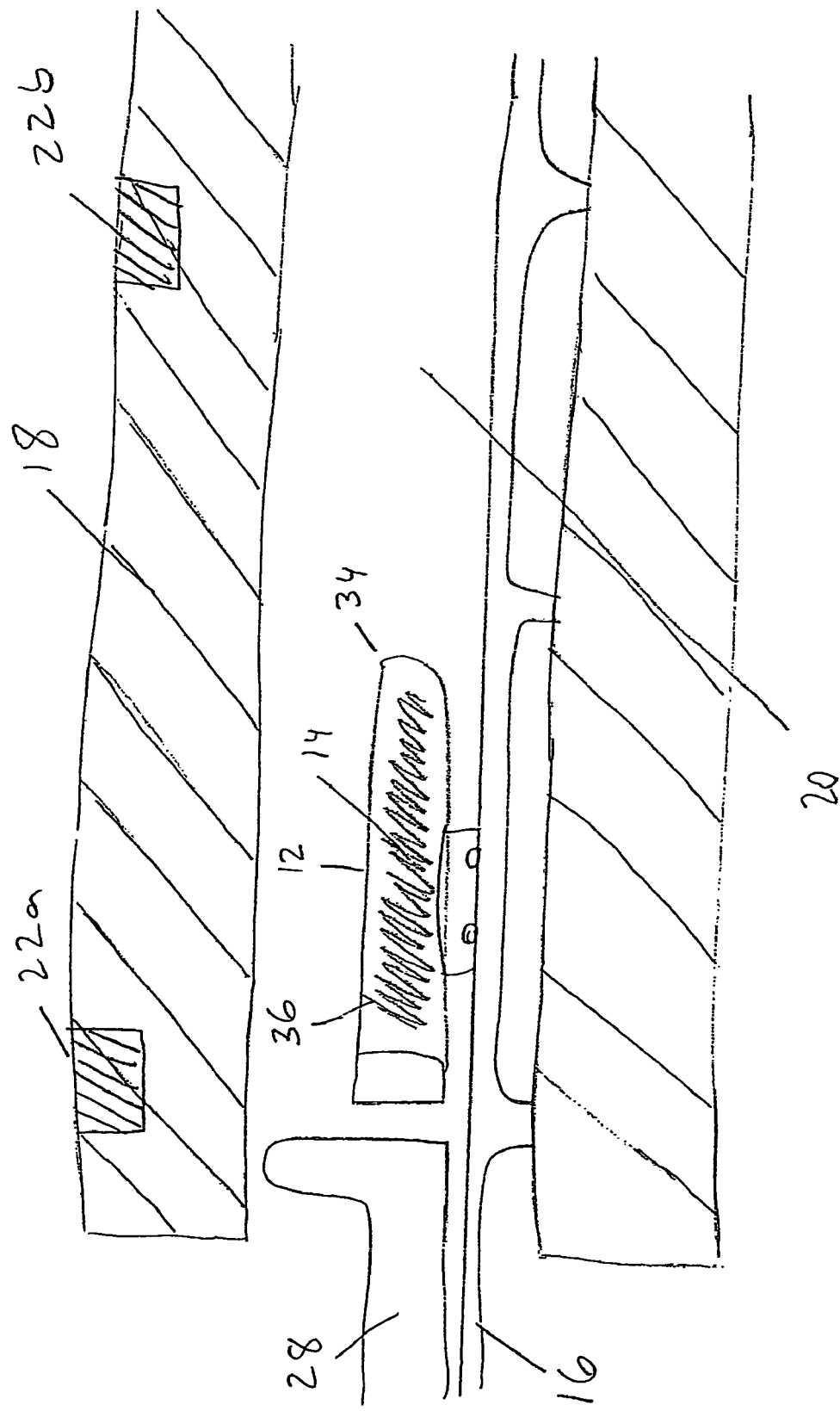
FIG. 1 (prior art) are schematic depictions of a directional cooling device.

The present invention is directed to a method and a device for the freezing of cells in solution so that the frozen cells can be lyophilized, stored and subsequently rehydrated. The principles and uses of the method according to the present invention may be better understood with reference to description, the experimental results and the drawings, in which like reference numerals refer to like parts throughout all of the figures. It is understood that the descriptions herein are illustrative and not intended to restrict the present invention to the specific details set forth below.

Figure 2:
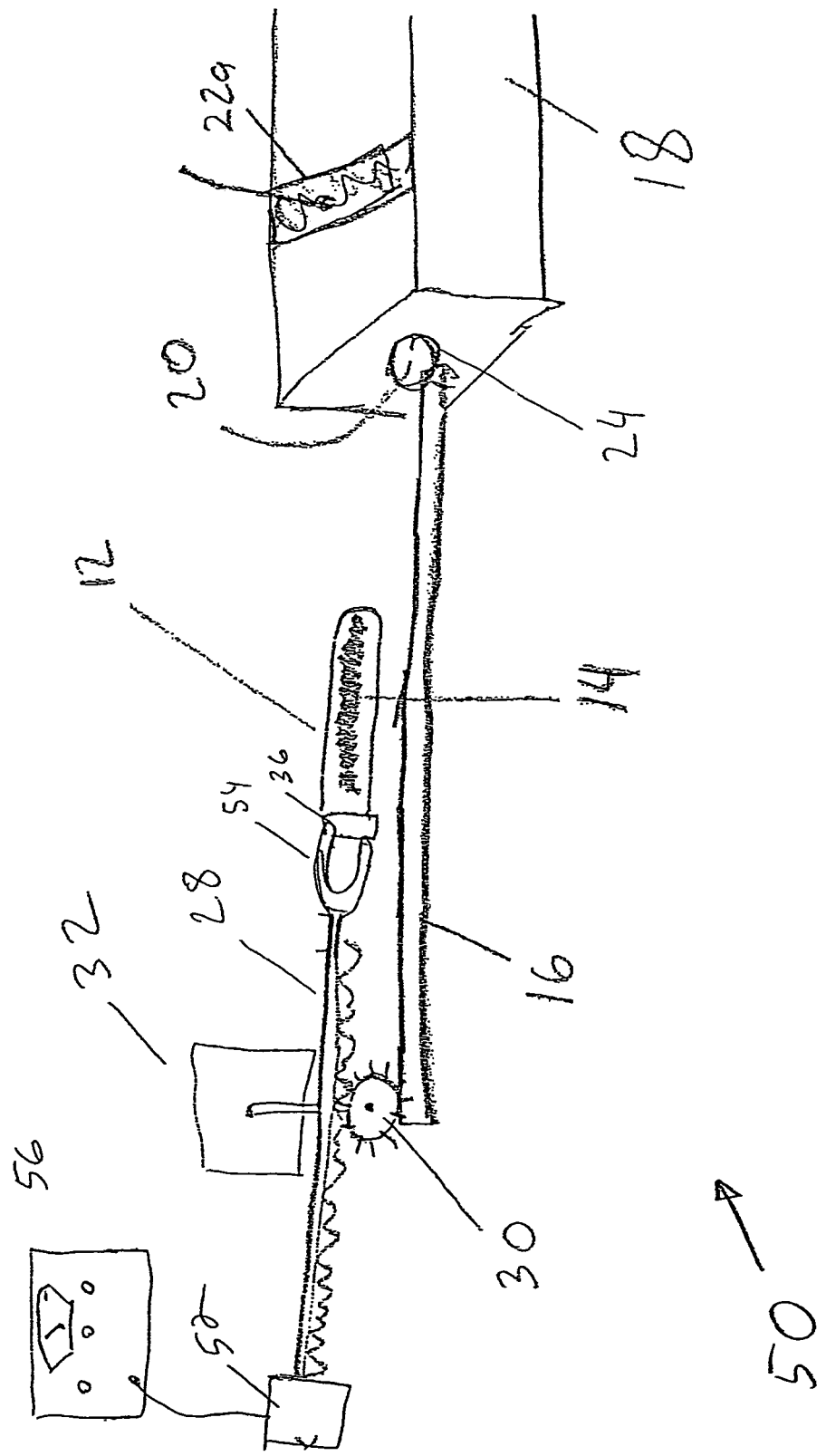
FIG. 2 is a schematic depiction of a cooling device of the present invention.

In FIG. 2 is depicted a cooling device 50 of the present invention. Clearly device 50 is similar to device 10 depicted in FIGS. 1. However, unlike in device 10, in device 50 rod 28 is tipped with engaging tines 54 and can be made to rotate around an axis parallel to track 16 by electrical rotation motor 52. The speed by which rotation motor 52 rotates rod 28 is determined by rotation controller 56. Engaging tines 54 are configured to engage following end 36 of vessel 12 when vessel 12 is on track 16.

When motor 32 is activated to cause rod 28 to push vessel 12 into tunnel 20, rotation motor 52 is also activated so as to rotate rod 28, engaging tines 54 and consequently vessel 12.

When the method of the present invention is used to freeze a sample, it is not necessary to add cryoprotectant to the sample. For a given sample, freezing according to the method of the present invention gives a significant improvement of post-thawing, and if lyophilized, post-rehydration cell viability when compared to freezing using the teachings of U.S. Pat. No. 5,873,254. That said, the method of the present invention is compatible with the use of cryoprotectants when and if desired.

In addition, due to the increased thermal homogeneity achieved by agitation of the sample-containing vessel, a much greater cooling rate (greater than 1° C./min and even greater than 50° C./min) can be used without reducing post-thawing or post-rehydration viability.

The advantages of the present invention can best be understood by considering two specific embodiments of the method of the present invention: freezing large volumes of a biological sample at one time and freezing biological samples as a step preceding lyophilization for long term storage of viable cells.

In a first embodiment of the present invention, large volumes of biological sample can be prepared for cryogenic storage at one time, a significant improvement of the teachings of U.S. Pat. No. 5,873,254. The much greater volumes that can be frozen are a result of the fact that agitation of the sample-containing vessel during the freezing process allows greater thermal homogeneity within the sample, allowing a vessel with a significantly greater diameter to be used. Experiments show that the largest practical vessel when using the teachings of U.S. Pat. No. 5,873,254 is about 5 cm long with a diameter of no more than about 0.5 cm. When using the teachings of the present invention, vessels with diameters of greater than 6 mm, and even diameters of greater than 25 mm, are typically used with no statistically significant reduction of post-rehydration viability. Increased sample volume coupled with a faster cooling rate described above allows for a significant throughput increase.

In a second embodiment of the present invention, freezing is a preparatory step for lyophilization. According to the present invention, when a sample is prepared for lyophilization, it is preferred that the vessel not be filled completely with biological sample. Preferred is that the biological sample fills only 90% of the vessel. more preferably only 50% of the vessel and most preferably only 30% of the vessel is filled. The frozen sample so produced has a very high surface area. The high surface area, as well as the fact that no cryoprotectant needs be added, means that subsequent lyophilization is quick and efficient. A combination of a high freezing-rate, high sample volume, and fast lyophilization allows for a significant throughput increase. More importantly, a sample lyophilized after being frozen according to the method of the present invention can be stored at relatively high temperatures for extended periods of time without significant post-hydration viability loss. In general storage temperature depends on the water loss. If a sample loses up to about 90% of the original weight due to lyophilization, the sample is stored at temperatures below freezing. If a sample loses more than about 90% of the original weight due to lyophilization, it may be possible to store the sample at high temperatures (277 K or even room temperature).

Rehydration of a sample lyophilized according to the method of the present invention is simple. After the sample is thawed in the usual way, a suitable liquid such as water is added.

Experimental Results

Unless otherwise noted, all materials were purchased from Sigma Inc. (St. Louis. Mo., USA).

Freezing and Lyophilization of Leukocytes

Leukocytes were separated from whole blood using Histopaque 1077. The samples were put in standard 15 ml test tubes and centrifuged for 30 minutes at 1000 G. The leukocyte layer was transferred to a different test tube and again centrifuged for 10 minutes at 250 G. The supernatant was discarded and the leukocyte pellet was washed with PBS and again centrifuged, as described above.

A leukocyte suspension was prepared by dissolving the leukocyte pellet in a solution containing 50% PBS (phosphate buffered solution) and 50% plasma. Trehalose was added so as to get a 0.1M trehalose concentration.

2.8 ml of the leukocyte suspension was transferred to each of three 12 ml glass test tube and frozen in a device of the present invention, a modified (resembling device 50 depicted in FIG. 2) MTG freezing apparatus manufactured by IMT, Israel. The thermal gradient in the cooling unit was set to 0.43° C./mm in all three cases with a final temperature of 203 K. The rate of test tube insertion (interface velocity) was 0.02, 0.2 and 2.0 mm/sec, yielding cooling rates of 0.5, 5.1 and 51° C./min, respectively. During insertion the test tubes were rotated at a rate of 32 rpm. Subsequent to freezing, a sample was taken from each test tube to test for cell viability, and the test tubes transferred to a lyophilizer. Lyophilization was performed at a chamber temperature of 238 K and a condenser temperature of 191 K for 3 hours and for 24 hours. A sample was taken from each test tube to test for viability after 3 hours lyophilization and after 24 hours lyophilization. After 24 hours of lyophilization test tube A lost 76% of the original sample weight, test tube B lost 77% of the original sample weight and sample C lost 87% of the original sample weight.

Each of the nine samples taken was allowed to thaw at room temperature and the cells rehydrated with distilled water. Viability was assessed using SYBR14/propidium iodide fluorescent staining (Molecular Probes Inc., Eugene, Oreg., USA). The viability results are summarized in Table 1.

TABLE 1

| test tube | Interface velocity [mm/sec] | Cooling rate [° C./min] | weight loss (%) | Viability (%) sample 1 (freeze/thaw) | sample 2 lyophilize (3 h) | sample 3 lyophilize (24 h) |
|---|---|---|---|---|---|---|
| A | 0.02 | 0.5 | 76 | 59 | 38 | 30 |
| B | 0.2 | 5.1 | 77 | 78 | 48 | 47 |
| C | 2 | 51 | 87 | 71 | 30 | 46 |

From the results presented in Table 1 it becomes clear that when it is desired to freeze-dry a large volume sample (in this case 2.8 ml) and preserve post-thaw viability, the method of the present invention gives remarkable results. Also seen is that the ideal interface velocity is very fast, indicating the usefulness of the present invention in a high throughput environment.

Four further identical test tubes, D, E, F and G were prepared as above to examine the influence of a different interface velocity at a cooling rate of 5.1° C./min cases to a final temperature of 253 K, 238 K, 203 K, 173 K, respectively. Samples were taken at intervals as described above. The test tubes were lyophilized to complete dryness (loss of greater than 92% of the initial weight) by lyophilization for 72 hours. After 72 hours lyophilization an additional sample was taken from each test tube. The results are presented in Table 2.

TABLE 2

| test tube | Interface velocity [mm/sec] | Viability (%) sample 1 (freeze/thaw) | sample 2 lyophilize (3 h) | sample 3 lyophilize (24 h) | sample 4 lyophilize (72 h) |
|---|---|---|---|---|---|
| D | 0.13 | 76 | 74 | 22 | 7 |
| E | 0.2 | 75 | 62 | 38 | 12 |
| F | 0.48 | 65 | 55 | 35 | 8 |
| G | 1.0 | 76 | 49 | 22 | 6 |

From the results in Table 2 it is seen that a high post-rehydration viability can be expected of cells dried according to the method of the present invention Six further identical test tubes were prepared as above to examine the influence of a different rotation velocities at a cooling rate of 5.1° C./min and an interface velocity of 0.2 mm/sec (test tubes H, I and J) to a final temperature of 203 K and 0.48 mm/sec (test tubes K, L and M) to a final temperature of 238 K. Samples were taken at intervals as described above. The results are presented in Table 3.

TABLE 3

| test tube | rotation rate [rpm] | Viability (%) sample 1 (freeze/thaw) | sample 2 lyophilize (3 h) | sample 3 lyophilize (24 h) | sample 4 lyophilize (72 h) |
|---|---|---|---|---|---|
| Interface velocity = 0.22 mm/sec | | | | | |
| H | 7 | 85 | 60 | 38 | 18 |
| I | 32 | 72 | 48 | 40 | 22 |
| J | 140 | 76 | 52 | 19 | 23 |
| interface velocity = 0.48 mm/sec | | | | | |
| K | 7 | 72 | 46 | 25 | 14 |
| L | 32 | 62 | 53 | 33 | 6 |
| M | 140 | 70 | 44 | 18 | 18 |

From the results in Table 3 it is seen that very good viability can be expected of completely dried cells. It is seen that when rotation is relatively fast, there is less viability loss between partial and complete drying, presumably due to better thermal homogeneity during freezing and drying.

While the invention has been described with respect to a limited number of embodiments, it will be appreciated that many variations, modifications and other applications of the invention may be made.

What is claimed is:

1. A device for freezing a sample comprising:
   a. a vessel for containing the sample;
   b. a mechanism for moving the vessel along a track;
   c. refrigeration means for imposing a laterally variable temperature gradient along the track, the refrigeration means including a plurality of thermally conductive blocks substantially enclosing the track, and
   means for agitating the vessel when moving along the track.

2. The device of claim 1 wherein said vessel is a tube with a diameter of greater than about 6 mm.

3. The device of claim 1 wherein said means of agitating said vessel includes a motor.

4. The device of claim 3 wherein said means of agitating said vessel includes an electrical motor.

5. The device of claim 1 wherein said means of agitating said vessel includes a control device to vary an intensity of agitation of said vessel.

6. The device of claim 1 wherein said means of agitating said vessel are means of rotating said vessel.

7. The device of claim 6 wherein an axis of rotation of said vessel caused by said rotating means is substantially parallel to said track.

8. The device of claim 6 wherein said means of rotating said vessel includes a motor.

9. The device of claim 8 wherein said means of rotating said vessel includes an electrical motor.

10. the device of claim 6 wherein said means of rotating said vessel includes a control device to vary a rate of rotation of said vessel.

11. A method for freezing cells comprising:
   a. confining a sample in a vessel, said vessel having a leading end and a terminal end, said sample containing the cells and having a freezing point; and
   b. gradually cooling said sample to below said freezing point so as to generate a temperature gradient in said sample, where during said cooling said leading end is cooler than said terminal end and to thus generate a freezing front moving from said leading end towards said terminal end;
   characterized in that during said gradual cooling said vessel is agitated.

12. The method of claim 11 wherein said agitation is rotation about an axis, said axis being substantially perpendicular to said freezing front.

13. The method of claim 11 wherein the sample is less than 100% of the internal volume of said vessel.

14. The method of claim 13 wherein the sample is less than about 90% of the internal volume of said vessel.

15. The method of claim 14 wherein the sample is less than about 50% of the internal volume of said vessel.

16. A method of freeze-drying cells comprising subsequent to freezing according to claim 11, said sample is lyophilized.

17. A method of storing viable freeze-dried cells comprising subsequent to said lyophilization according to claim 16, storing said sample at a storage temperature for a period of time, said storage temperature being greater than about 193 K.

18. The method of claim 17, wherein said storage temperature is greater than about 253 K.

19. The method of claim 18, wherein said storage temperature is greater than about 273 K.

20. The method of claim 17 wherein said sample includes a cryoprotectant, said cryoprotectant being a solid at said storage temperature.

21. The method of claim 20 wherein said cryoprotectant is trehalose.

22. The method of claim 17 wherein said period of time is greater than about 1 day.

23. The method of claim 22 wherein said period of time is greater than about 1 week.

24. The method of claim 23 wherein said period of time is greater than about 6 weeks.

25. A device for freezing a sample comprising:
   vessel for containing the sample, the vessel comprising a cooling front;
   a mechanism for moving the vessel along a track in a direction of advancement; and
   refrigeration means for imposing a laterally variable temperature gradient along the track, the refrigeration means including a plurality of thermally conductive blocks substantially enclosing the track, and
   means for agitating the vessel on an axis substantially parallel to the direction of advancement and substantially perpendicular to the cooling front of the vessel when moving along the track.

26. The device of claim 1, wherein the means for agitating the vessel is configured sufficient to agitate the vessel on an axis substantially perpendicular to a direction of movement of the vessel along the track.

27. The device of claim 26, wherein agitating comprises rotation.

* * * * *